United States Patent [19]

Chamberlain, Jr. et al.

[11] Patent Number: 5,041,215
[45] Date of Patent: Aug. 20, 1991

[54] DIALYSIS UNIT PRIMING

[75] Inventors: Leonard D. Chamberlain, Jr., Boulder; Donn D. Lobdell, Englewood, both of Colo.

[73] Assignee: Cobe Laboratories, Inc., Lakewood, Colo.

[21] Appl. No.: 440,330

[22] Filed: Nov. 22, 1989

[51] Int. Cl.[5] .................. B01D 61/28; B01D 61/30
[52] U.S. Cl. ................................ 210/136; 210/239; 210/321.72; 210/406
[58] Field of Search .............. 210/136, 239, 321.69, 210/321.72–321.81, 406

[56] References Cited

U.S. PATENT DOCUMENTS 4,209,402  6/1980  Gentles ...................... 210/321.69

FOREIGN PATENT DOCUMENTS

WO/851038-79  9/1985  PCT Int'l Appl. .

Primary Examiner—W. Gary Jones

[57] ABSTRACT

Dialysis unit with vacuum removal therethrough of priming saline and selective circulation therethrough of dialysate and other fluids. The dialyzer unit includes a drain configured to sealingly cooperate with a tubing set having a cap with a central conduit portion and sealing fins for cooperating with the drain, and a venturi in a main effluent passage in fluid communication with the drain.

19 Claims, 4 Drawing Sheets

DIALYSIS UNIT PRIMING

FIELD OF THE INVENTION

This invention relates to dialysis units, and more particularly to provision therein of improved saline disposal.

BACKGROUND OF THE INVENTION

It is known to prime a dialysis unit with saline, connecting a tubing set between a saline bag and a waste bucket.

SUMMARY OF THE INVENTION

A dialysis unit may provide for saline disposal through conduits of the unit.

In preferred embodiments, a drain is selectively cooperative with an ordinary operating hydraulic circuit and a saline priming circuit; the ordinary operating circuit includes a handle longitudinally and rotationally movable between a position implementing the ordinary operating hydraulic circuit and a position implementing a saline priming circuit; the saline priming circuit includes a cap selectively engageable with the drain; and both circuits include means to create vacuum therethrough.

PREFERRED EMBODIMENT

The presently preferred embodiment is shown in the drawings, and its structure and operation then described.

DRAWINGS

STRUCTURE

Turning now to the drawings, there is indicated generally at 10 a dialysis unit.

Figure 1:
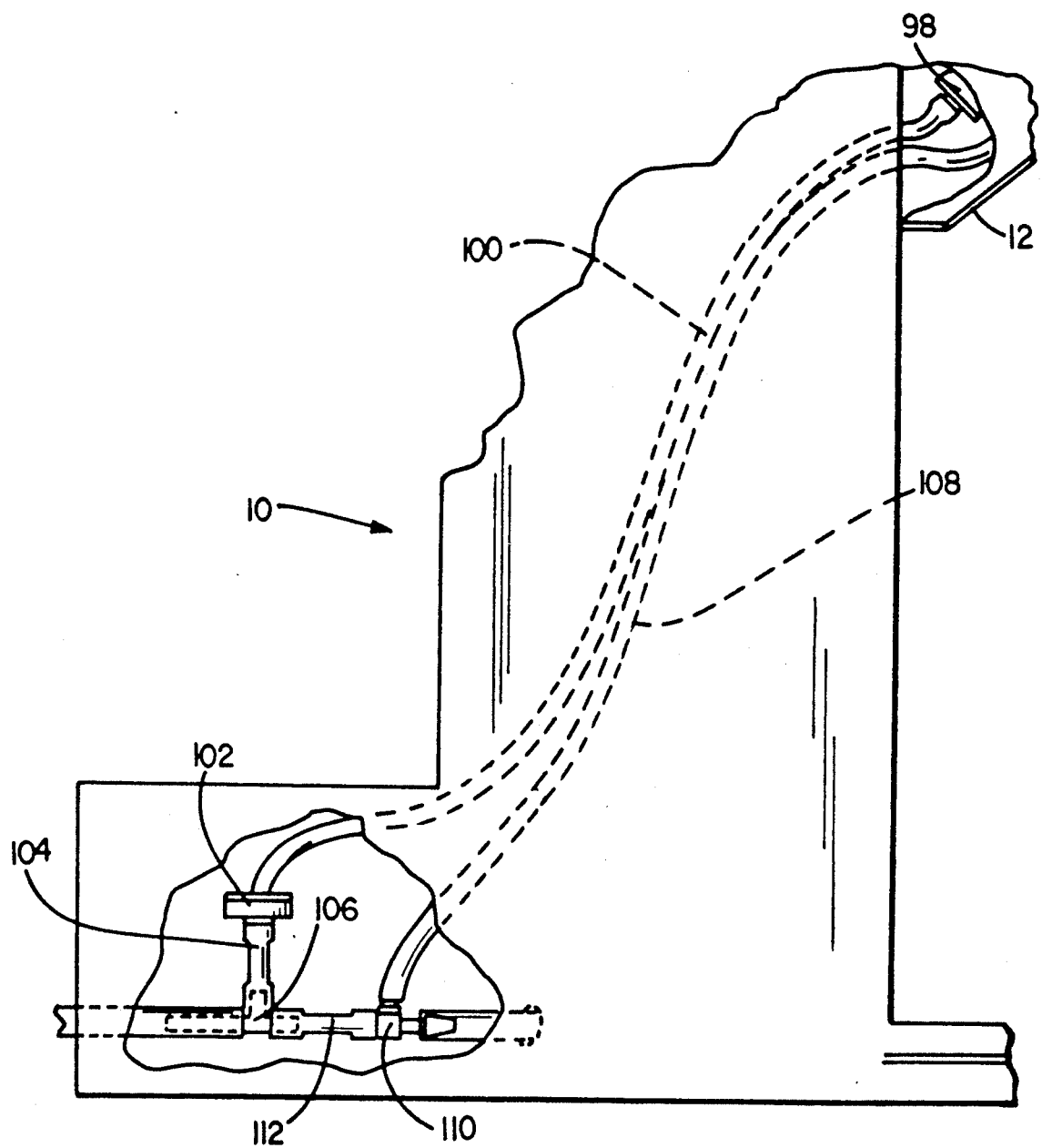
FIG. 1 is an end elevation view, broken away in several respects, of the presently preferred embodiment of the invention.
Figure 2:
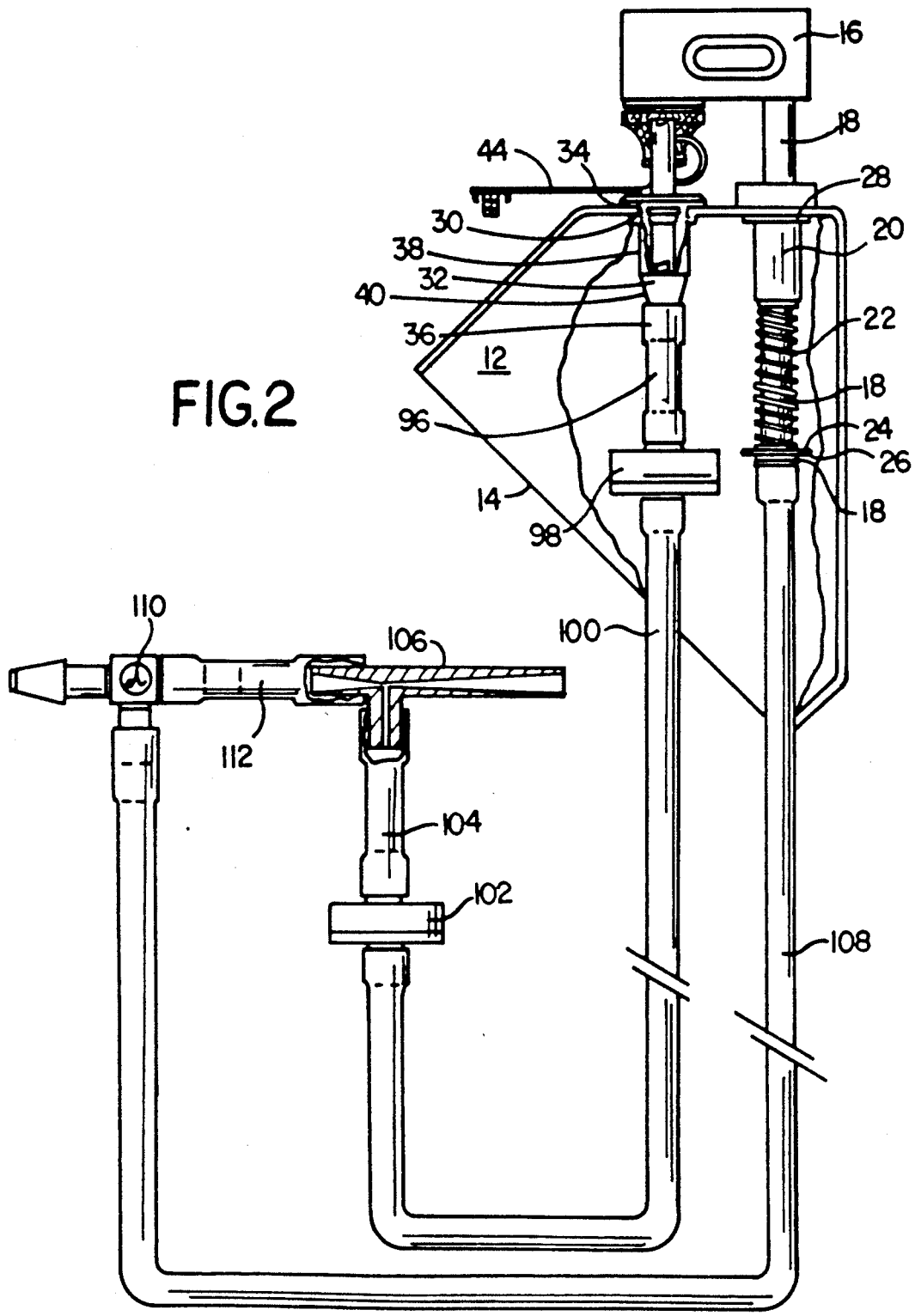
FIG. 2 is a somewhat diagrammatic view of a portion of said embodiment.
Figure 3:
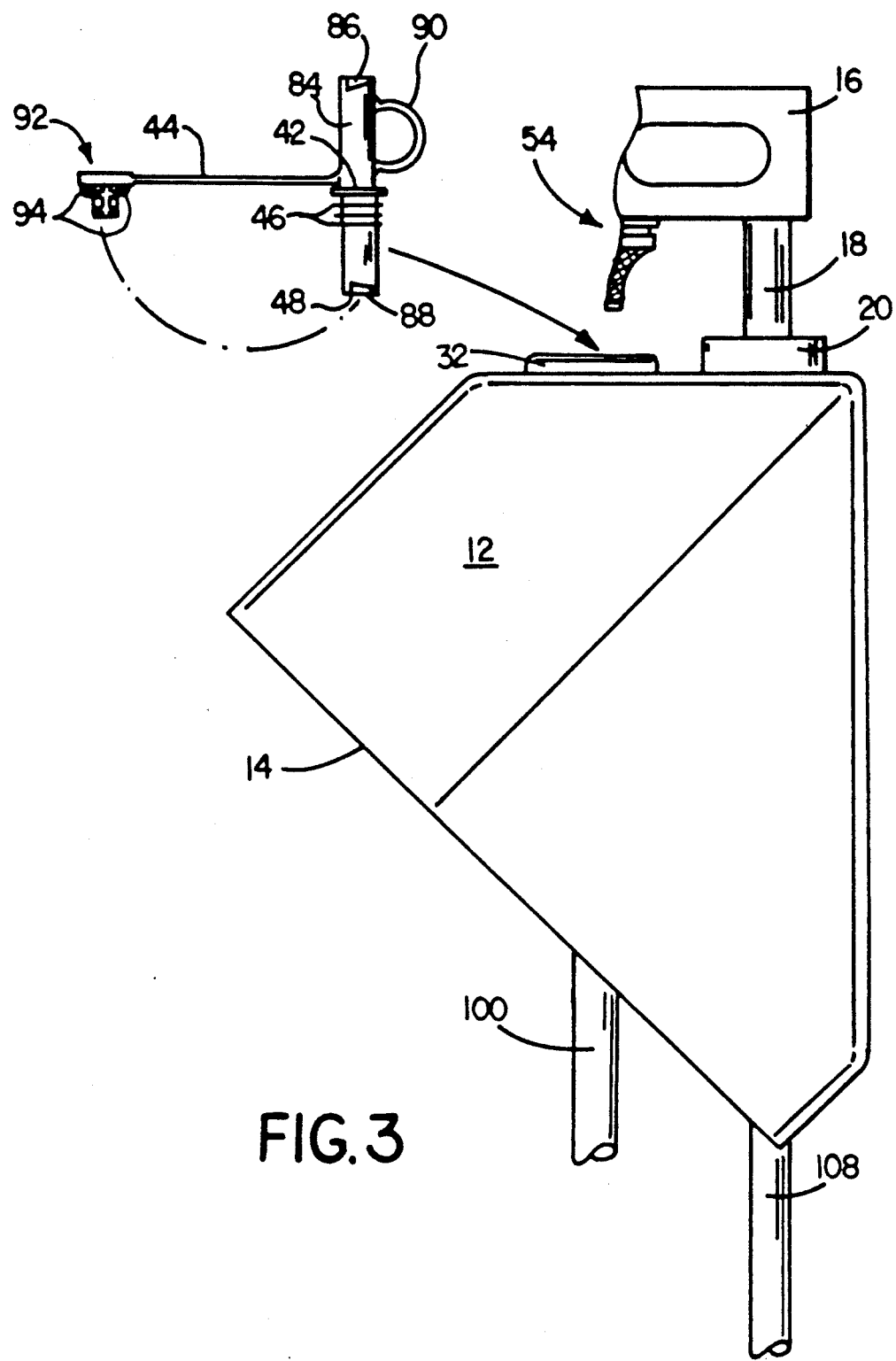
FIG. 3 is a view, partially broken away, of a portion of the portion shown in FIG. 2.

Mounted on the control panel portion of the dialysis unit 10 by means not shown is waste handling housing 12, which is shown in FIGS. 2 and 3, somewhat diagrammatically, as having its panel contact rim 14 at an angle, while in fact the rim lies in a vertical plane, for engagement therein with the control panel portion above mentioned.

Handle 16 is fixedly secured to shaft 18 which is axially movable relative to bushing 20 mounted on housing 12. Shaft 18 is biased toward housing 12 by spring 22, which is compressed between bushing 20 and washer 24 supported by snap ring 26 carried in a groove in shaft 18.

Bushing 20 has within it camming surfaces (not shown) which cooperate with pins on shaft 18 (not shown) to rotate handle 16 so as to align the axes of valve unit 54 and drain 32, when the handle is not prevented from such movement (as, by insertion of a cap 44 in the drain).

Snap ring 28, carried in a groove in bushing 20, retains bushing 20 in housing 12.

Also retained in housing 12, by snap ring 30 in a groove therein is drain 32, which includes integrally portion 34, a slightly smaller diameter portion 38, a frustoconical portion 40, and a smallest diameter portion 36. Internally, drain 32 contains a counterbore in which seats seating fin 42 of priming cap 44. The hole in drain 32 adjacent said counterbore is of diameter to sealingly accept sealing fins 46 of cap 44, and of depth so that the end 48 of cap 44 does not reach it.

Figure 4:
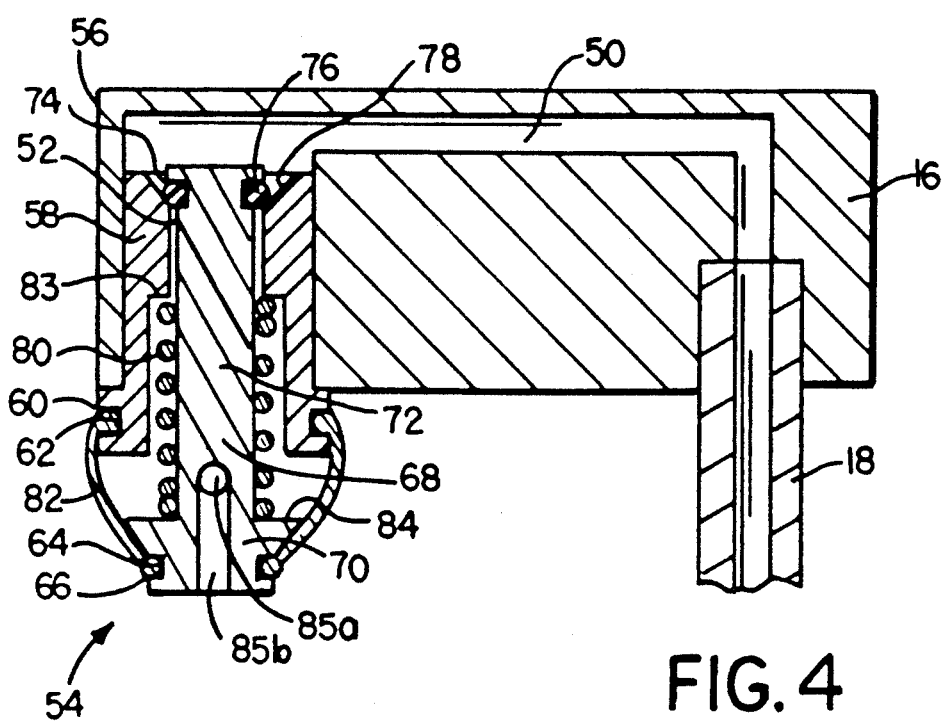
FIG. 4 is a vertical sectional view through upper portions of the portion shown in FIG. 2.

Handle 16 is an integral plastic piece carrying three holes. One, counterbored, shown in FIG. 4, carries stem 18. Hole 50, ⅛ inch in diameter, connects the hole from stem 18 with hole 52 through valve unit indicated generally at 54. Hole 50 is done by drilling, followed by plugging the hole so as to produce the imperforate wall 56 as shown in FIG. 4.

Cap 44, as best shown in FIG. 3, is Dowlex 2535 LLDPE injection molded in one piece. Longitudinal portion 84 has extending through its length a hole, defined by two female luer portions intersecting longitudinally centrally thereof. Luer threads 86, 88 are provided. Loop 90 permits hanging on IV poles. There is provided breather cap portion 92, with longitudinal grooves and a pair of notched fins which in combination force air to make three 90° turns. There are also a pair of catches 94.

Referring now to FIG. 2, from drain 32 extends tubing 96, into check valve 98, from which tubing 100 extends to check valve 102, from which tubing 104 extends into the sidearm of venturi 106.

The lower end of shaft 18 is connected into tubing 108, which extends to tee 110, connected also by tubing 112 to venturi 106.

Valve unit 54 includes plastic body 58 with circumferential groove 60 carrying circumferential lip 62 of silicone rubber boot 82, circumferential lip 64 of which is seated in circumferential groove 66 of stem 68. The stem 68 is of ABS plastic, and includes the larger portion 70 which carries groove 66, the smaller diameter portion 72 which extends for most of its length, and circumferential groove 74 in which is seated O-ring 76, which in turn is seated in chamfer 78. Spring 80 is compressed between surface 83 of body 58 and surface 84 of stem 68. The boot 82 has a thickness between lips of 1/64 of an inch. A right-angled hole with portions 85a and 85b is provided in stem 68.

OPERATION

In use, fluid constantly flows through dialysis unit 10, whether for example water, dialysate, or bleach. This effluent constantly moves through tee 110, tubing 112, venturi 106, and out through exit conduit not shown.

Except when it is desired to prime, by filling dialyzer and tube set with saline, valve unit 54 (FIG. 3) is seated in place in drain 32. The action of spring 22 in pulling handle 16 down causes the lower surface of stem 72 to engage the counterbore in drain 32 already referred to and move up stem 72, moving O-ring 76 out of valving engagement with chamfer 78.

The vacuum pulled in the sidearm of venturi 106 by the flow through it already mentioned then draws a portion of that flow through the loop consisting of, successively, tee 110, tubing 108, stem 18, handle 16 through the open valve unit 54, down the drain 32, continuing with tubing 96, check valve 98, tubing 100, check valve 102, tubing 104, through venturi 106 to mingle with mainstream effluent. In this mode of operation, no cap 44 (which would prevent the rotational stem 18 movement above mentioned) is in place.

When saline priming is desired, handle 16 is moved upward by hand, and rotated to permit insertion of cap 44, as shown in FIG. 3. This, through the action of spring 80, no longer overridden by the drain counterbore surface above mentioned, closes the O-ring 76 valve in valve unit 54 and stops flow in the circuit above enumerated.

Desirably, tube sets are provided with at least one cap 44 already in place, for insertion as above described. The other end is then spiked into a saline bag (preferably using as a connector, although its other functions are there irrelevant, a cap 44). Saline is then drained through that portion of the loop above enumerated between drain 32 and the sidearm of venturi 106.

The invention thus provides for clean, easy, and safe disposal of waste saline.

Inclusion as described of the vacuum means insures that whenever there is a change from priming mode to other mode, or the reverse, the downstream line to which connection is selectively made is empty.

Contamination between patients is prevented by a number of features. During priming, the blood pump turns backward, so that pressure is adverse to backflow into the tubing set. Further insurance thereagainst is provided by check valves 98 and 102. The cap 44 used to connect a tubing set to the drain is to be used only once. Even if by mistake it is used a second time, its configuration as above described prevents contamination. Because of the fins 46 and the spacing of the end 48, the fluid passages of the tubing set are never in contact with the dialysis unit 10. The entire fluid circuit is cleaned and disinfected after each patient.

OTHER EMBODIMENTS

Other embodiments within the invention will occur to those skilled in the art.

The vacuum means may be, for example, an orifice plate rather than a venturi.

What is claimed is:

1. A dialysis unit comprising
a tubing set connected to a dialyzer,
a drain configured to sealingly cooperate with said tubing set,
a cap carried by said tubing set for sealingly cooperating with said drain and detachably connecting said tubing set to said drain,
said cap including a central conduit portion and sealing means therearound for sealingly cooperating with said drain.

2. The unit of claim 1 which includes also an operating mode connector selectively sealingly engageable with said drain.

3. The unit of claim 2 in which said connector is externally configured as a handle.

4. The unit of claim 2 in which said connector is longitudinally and circumferentially movable relative to the rest of said unit.

5. The unit of claim 2 in which said connector includes a valve unit.

6. The unit of claim 5 in which said connector is a part of a second fluid circuit portion including passage means through said valve unit and from said valve unit.

7. The unit of claim 6 in which said valve unit includes means engageable with said drain for opening a valve in said valve unit when said valve unit is introduced into said drain.

8. The unit of claim 6 in which said valve unit includes an elastomeric boot engageable with said drain.

9. The unit of claim 1 in which said drain is in a first fluid circuit portion including a main effluent passage of said unit.

10. The unit of claim 9 in which said first fluid circuit portion includes vacuum means applying a reduced pressure to said drain.

11. The unit of claim 9 which includes at least one check valve oriented to prevent movement of fluid toward said drain.

12. A dialysis unit comprising a drain,
a tubing set configured to sealingly cooperate with said drain,
said tubing set carrying a cap for sealingly cooperating with said drain,
said cap including a central conduit portion and a plurality of sealing fins therearound.

13. The unit of claim 12 in which said cap is integrally constituted of plastic.

14. The unit of claim 12 in which said cap includes around said portion a stop for cooperating with said drain to longitudinally position said cap in said drain.

15. The unit of claim 14 which said stop positions said cap so that an inner end of said conduit portion is spaced from and out of contact with said drain.

16. A dialysis unit comprising
a drain configured to sealingly cooperate with a tubing set,
said drain being in a first fluid circuit portion including a main effluent passage of said unit,
said first fluid circuit portion including vacuum means applying a reduced pressure to said drain,
said vacuum means being a venturi situated in said main effluent passage and with a sidearm in fluid communication with said drain.

17. A dialysis unit comprising
a drain configured to sealingly cooperate with a tubing set, and
an operating mode connector selectively sealingly engageable with said drain,
said connector including a valve unit,
said drain being in a first fluid circuit portion including a main effluent passage of said unit,
said connector being a part of a second fluid circuit portion including passage means through said valve unit and from said valve unit,
said second fluid circuit portion being connected into said main effluent passage.

18. A dialysis unit comprising
integral drain circuit means having a first circuit portion with an inlet and an outlet,
said drain circuit means including a main effluent passage to which said outlet is connected,
said inlet being configured to detachably and sealingly connect to a tubing set to provide for draining of said tubing set when said tubing set is connected to said inlet, and
a second circuit portion that is connected to said main effluent passage at one end and is selectably sealingly connectable to said inlet at another end to provide for recirculating flow through said first and second circuit portions when said another end is connected to said inlet.

19. A tubing set for connecting a dialyzer in a dialysis unit comprising
tubing, and
a cap carried by said tubing for sealingly cooperating with a drain of said dialysis unit and detachably connecting said tubing to said drain,
said cap including a central conduit portion and a plurality of sealing fins therearound for sealingly cooperating with said drain.

* * * * *